(12) United States Patent  (10) Patent No.: US 8,390,452 B2
Blake et al.  (45) Date of Patent: Mar. 5, 2013

(54) COLOR CODED RFID TAGS FOR SURGICAL INSTRUMENTS

(75) Inventors: Kenneth R. Blake, Brooklyn Park, MN (US); Timothy M. Scanlan, St. Paul, MN (US)

(73) Assignee: Scanlan International, Inc., St. Paul, MN (US)

( * ) Notice: Subject to any disclaimer, the term of this patent is extended or adjusted under 35 U.S.C. 154(b) by 590 days.

(21) Appl. No.: 12/055,979

(22) Filed: Mar. 26, 2008

(65) Prior Publication Data

US 2008/0238631 A1 Oct. 2, 2008

Related U.S. Application Data

(60) Provisional application No. 60/920,662, filed on Mar. 29, 2007.

(51) Int. Cl.
 *G08B 13/14* (2006.01)
 *G06F 19/00* (2011.01)
 *A61B 5/00* (2006.01)

(52) U.S. Cl. ............ 340/572.1; 340/539.12; 340/539.13; 235/385; 40/299.01; 40/633; 40/638; 40/661.09

(58) Field of Classification Search ................ 340/572.1
 See application file for complete search history.

(56) References Cited

U.S. PATENT DOCUMENTS

| 2005/0108912 A1* | 5/2005 | Bekker ........................... 40/633 |
| 2006/0109118 A1* | 5/2006 | Pelo et al. ................... 340/572.1 |
| 2006/0244597 A1* | 11/2006 | Tethrake et al. ........... 340/572.1 |

OTHER PUBLICATIONS

Surg-I-Band Color Coding, Scanlan International website, copyright 2006, 2 pages.

* cited by examiner

*Primary Examiner* — Donnie Crosland

(74) *Attorney, Agent, or Firm* — Faegre Baker Daniels LLP

(57) ABSTRACT

Color coding tape having one or more RFID tags are attached to surgical instruments or other medical devices. Information relating to the medical devices can be written to and/or read from the RFID tags. The medical devices can be usually identified by the color coding tape.

11 Claims, 1 Drawing Sheet

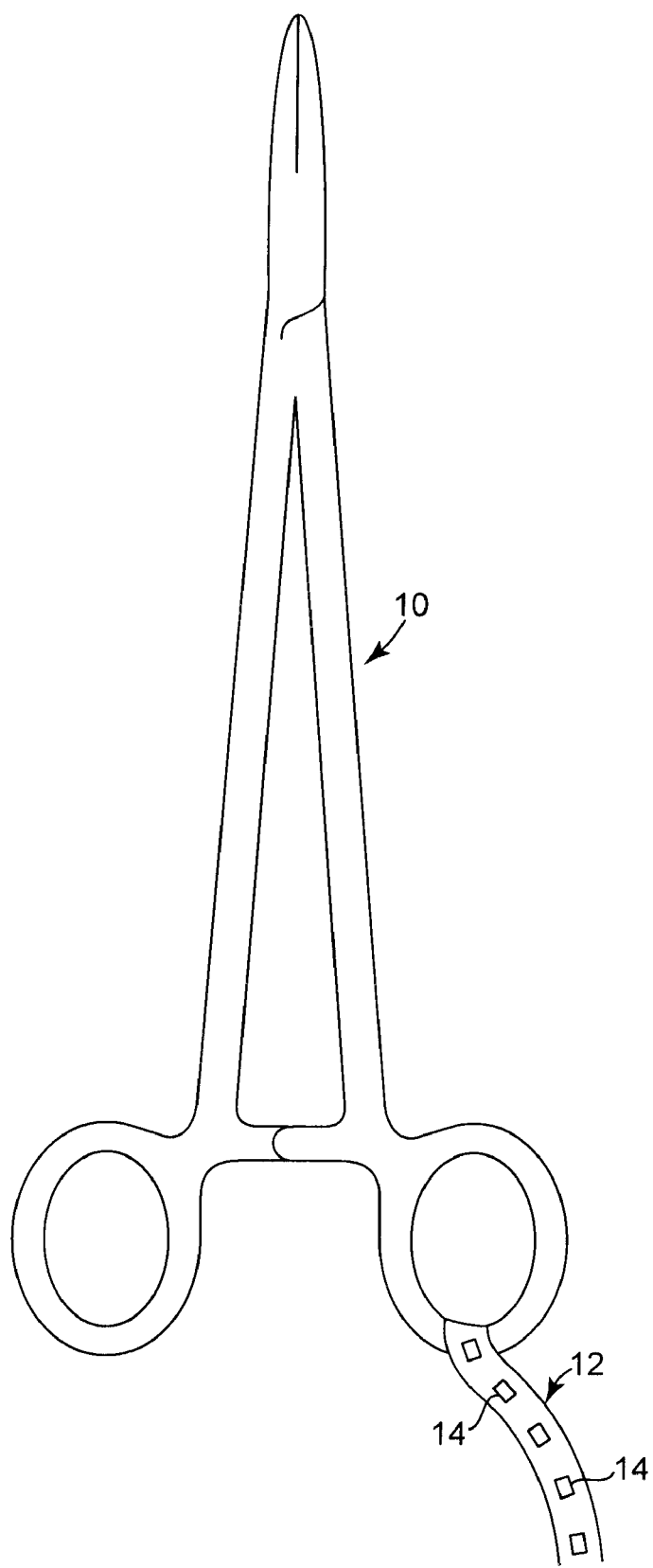

COLOR CODED RFID TAGS FOR SURGICAL INSTRUMENTS

REFERENCE TO RELATED APPLICATION

This application claims the benefit of U.S. Provisional Application Ser. No. 60/920,662, filed Mar. 29, 2007 and entitled COLOR CODED RFID TAGS FOR SURGICAL INSTRUMENTS, which is incorporated herein by reference.

FIELD OF THE INVENTION

The invention relates generally to systems for identifying and tracking equipment such as surgical instruments used in surgical and medical applications.

BACKGROUND OF THE INVENTION

The identification and tracking of surgical instruments and other equipment used in surgical and medical applications is difficult and time consuming. Many of the personnel handling the equipment are minimally educated regarding the application of the equipment, common name, or correct routing through cleaning and preparation for use. Tracking of the equipment to assure proper maintenance, use-life schedule, and location is also difficult. These tasks are generally accomplished through manual record keeping, visual inspection, and processing of all items grouped together without specific item identification. Identification of the equipment is provided through visual marking, either by mechanical etching, coating of a portion of the equipment with a colored plastic film, or identification with a color coding "band" such as the Surg-I-Band color coding system available from Scanlan International of St. Paul, Minn. These methods provide for non-specific identification or group recognition in a variety of use and preparation areas.

With the development of cost effective electronic identification technology several methods have become adopted to provide specific and unique tracking of medical equipment. Limitations include the necessity of applying a label containing the information (bar coding/2D labeling) and access to a "reader" to translate the information. More recently RFID (radio frequency identification) has become adapted for the identification and tracking of some medical equipment. RFID tags are placed on devices and used to record the movement through the use and maintenance cycle of the device. The difficulty with this technology is placement onto new devices. An even greater challenge is the attachment to and implementation of this technology to the entire capital base of equipment currently in use throughout the medical care industry.

SUMMARY OF THE INVENTION

One embodiment of the invention is color coding tape having one or more RFID tags. Another embodiment of the invention is a medical device such as a surgical instrument including the color coding tape and RFID tags. Tracking and/or identification information can be written to and/or read from the RFID tags. Instruments and medical devices in accordance with the invention can be rapidly visually identified by the color coding tape. Other relevant information stored on the RFID tags can be processed electronically.

BRIEF DESCRIPTION OF THE DRAWINGS

FIG. 1 is an illustration of a surgical instrument having a color coding band with an RFID tag in accordance with one embodiment of the invention.

DESCRIPTION OF THE INVENTION

To provide for both electronic and traditional visual identification, a unique combination of the RFID technology and a self-applied color coding band is applied to the instrument and/or other medical devices. This provides for rapid visual identification by multiple handlers and users of surgical instruments as well as electronic identification and tracking. Surgical instruments and medical devices that would find practical application for this invention include scalpels, rongeurs and other orthopedic instruments, clamps, scissors, needle holders, graspers, forceps, punches, and many others, all of which are available in a variety of styles and designs unique to each surgical application.

The implanted RFID tag is placed within the color coding band to preserve its ability to be read by the reader equipment preserving all of the features of this technology. FIG. 1, for example, illustrates a surgical instrument 10 having a color coding band 12 with RFID tags 14. Inventory tracking, identification, location recording, use life and maintenance recording are all part of this identification system. Placement of the RFID tag within the color coding band can be accomplished through one of several methods. Methods include automated placement of the tag onto a layer of plastic film at a specific location and an additional film placed over the first film and either laminated and joined together with an adhesive or through a heating and/or pressure process. An alternative method includes extruding a plastic material with the RFID tag placed within the extruded material during the extrusion process. Although more than one RFID tag 14 is shown in the embodiment in FIG. 1, other embodiments (not shown) have fewer (e.g., one) or greater numbers of RFID tags.

The user may remove and apply the color coding band containing the RFID tag as desired to any surgical product. The newly applied color coding containing the RFID tag can either be preprogrammed with the desired data/information or the RFID tag can be programmed at the time of placement. This provides for easy changing of the current tagged color coding to relocate the device to a different area or application. This ease of use also provides an opportunity to place the RFID technology on the over 30 million surgical instruments and devices in use throughout the hospital and health care system.

The unique and superior qualities of the Scanlan Surg-I-Band color coding are preserved with this invention allowing quick visual identification by device handlers and users without the need for a reader device. Much of the handling of these instruments and devices are done in rapid use situations and transferred throughout areas of the health care facility. Visual identification provides for efficient handling, sorting and application of use.

The use and care environment of surgical and medical devices is severe involving contact with body fluids, cleaning agents and sterilization processing. The unique, long proven use of the Scanlan Surg-I-Band color coding provides stability in all of these environments for long periods of time.

The use of materials within medical and surgical applications requires compliance with sophisticated government and healthcare regulations. The Scanlan Surg-I-Band color coding product is fully compliant with standards defined and referred by the US FDA, the European Medical Device Directives and many other professional and international standards.

Although the present invention has been described with reference to preferred embodiments, those skilled in the art will recognize that changes can be made in form and detail without departing from the spirit and scope of the invention.

What is claimed is:

1. A plurality of elongated, flexible adhesive-backed strips of color coding tape configured for removable adhesive attachment to a hand-operated surgical instruments, each of the strips of color coding tape having one or more RFID tags within the tape, wherein the one or more RFID tags are programmed with identification information and wherein each of the strips of tape has a different color to provide visual instrument identification information.

2. The tape of claim 1 and adhesive for securing the one or more RFID tags to the color coding tape.

3. The tape of claim 1 and an encapsulant for covering the one or more RFID tags.

4. A method for using the tape of claim 1, including writing information to the one or more RFID tags.

5. The method of claim 4, further including reading information from the one or more RFID tags.

6. A method for using the tape of claim 1, including reading information from the one or more RFID tags.

7. The color coding tape of claim 1 and further including one or more of tracking and identification information recorded on the one or more RFID tags.

8. An assembly including:
a hand-operated surgical instrument;
an elongated, flexible, adhesive-backed strip of a color coded tape adhesively and removably attached to the surgical instrument, the color coded tape having one or more RFID tags within the tape, and wherein the one or more RFID tags are programmed with identification information and a color of the color coding tape provides visual instrument identification information.

9. A method for using the assembly of claim 8, including writing information to the one or more RFID tags.

10. The method of claim 9, further including reading information from the one or more RFID tags.

11. A method for handling a surgical instrument including:
providing a hand-operated surgical instrument;
providing a plurality of elongated, flexible, adhesive-backed strips of color coded tape having one or more RFID tags within the tape;
selecting and obtaining from the plurality of strips of tape a piece of the color coded tape having a color corresponding to instrument identification information associated with the surgical instrument;
programming the one or more RFID tags within the color coded tape with instrument identification information associated with the surgical instrument;
adhesively attaching the selected piece of color coded tape to the surgical instrument; and
removing the piece of the color coded tape from the surgical instrument.

* * * * *

UNITED STATES PATENT AND TRADEMARK OFFICE
CERTIFICATE OF CORRECTION

| | | |
|---|---|---|
| PATENT NO. | : 8,390,452 B2 | Page 1 of 1 |
| APPLICATION NO. | : 12/055979 | |
| DATED | : March 5, 2013 | |
| INVENTOR(S) | : Kenneth R. Blake et al. | |

It is certified that error appears in the above-identified patent and that said Letters Patent is hereby corrected as shown below:

In the Specifications:

Column 3, line 8, delete "a"

Signed and Sealed this
Fourteenth Day of May, 2013

Teresa Stanek Rea
*Acting Director of the United States Patent and Trademark Office*